(12) United States Patent
Strocchia-Rivera

(10) Patent No.: US 9,459,226 B2
(45) Date of Patent: Oct. 4, 2016

(54) LENS COATING/CONTAMINATION ELECTRONIC DETECTION

(71) Applicant: International Business Machines Corporation, Armonk, NY (US)

(72) Inventor: Carlos Strocchia-Rivera, Highland, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 372 days.

(21) Appl. No.: 14/024,740

(22) Filed: Sep. 12, 2013

(65) Prior Publication Data

US 2015/0070032 A1   Mar. 12, 2015

(51) Int. Cl.

| | |
|---|---|
| *G01R 27/26* | (2006.01) |
| *G01N 27/24* | (2006.01) |
| *G01N 27/22* | (2006.01) |
| G01N 27/20 | (2006.01) |
| G01N 21/55 | (2014.01) |
| G01N 21/15 | (2006.01) |

(52) U.S. Cl.
CPC .............. *G01N 27/24* (2013.01); *G01N 27/22* (2013.01); *G01N 21/55* (2013.01); *G01N 27/20* (2013.01); *G01N 2021/155* (2013.01)

(58) Field of Classification Search
CPC ...... G01N 27/22; G01N 27/24; G01N 27/20; G01N 27/221
USPC .................................................. 324/663, 686
See application file for complete search history.

(56) References Cited

FOREIGN PATENT DOCUMENTS

GB              2185578 A  *  7/1987  .............. G01J 5/041

* cited by examiner

*Primary Examiner* — Amy He
(74) *Attorney, Agent, or Firm* — Yuanmin Cai; Andrew M. Calderon; Roberts Mlotkowski Safran Cole & Calderon, P.C.

(57) ABSTRACT

A contamination detection apparatus may include an optical element having an outer surface and an other surface opposing the outer surface, a first capacitor plate located on the outer surface at an outer periphery of the optical element, and a second capacitor plate located on the outer surface at the outer periphery of the optical element. The second capacitor plate is located adjacent the first capacitor plate and separated from the first capacitor by a gap to form a capacitor, whereby a contaminant is electrically detected based on the contaminant entering the gap and varying a capacitance value corresponding to the capacitor.

17 Claims, 7 Drawing Sheets

LENS COATING/CONTAMINATION ELECTRONIC DETECTION

BACKGROUND a. Field of the Invention

The present invention generally relates to optical systems, and more particularly to detecting contamination within such optical systems.

b. Background of Invention

Optical metrology and inspection equipment such as, for example, reflectometers may often use high power optical lens/objectives in close proximity to surfaces for measurement and/or inspection purposes. In manufacturing environments these surfaces may often release gases or vapors that can coat the lens/objectives in such a manner that light collected by these lens/objectives is distorted and/or attenuated. The measurement and/or inspection results may thus be distorted as a result of the measurement being influenced by the existing contamination.

BRIEF SUMMARY

According to one or more embodiments, it may therefore, be advantageous, among other things, to electronically detect contaminants (e.g., gases/vapors) that may coat the optical components (e.g., lenses) of equipment (e.g., reflectometer systems, photolithographic systems) in order to determine the authenticity of the measurements or collected data.

According to at least one exemplary embodiment, a contamination detection apparatus may include an optical element having an outer surface and an other surface opposing the outer surface, a first capacitor plate located on the outer surface at an outer periphery of the optical element, and a second capacitor plate located on the outer surface at the outer periphery of the optical element. The second capacitor plate is located adjacent the first capacitor plate and separated from the first capacitor by a gap to form a capacitor, whereby a contaminant is electrically detected based on the contaminant entering the gap and varying a capacitance value corresponding to the capacitor.

According to at least one other exemplary embodiment, a method of determining contamination over an outer surface of a final stage optical element of an optical system is provided. The method may include applying an alternating signal having a predetermined voltage amplitude to a first capacitor plate located on the outer surface at an outer periphery of the optical element, and applying a ground signal to a second capacitor plate located on the outer surface at the outer periphery of the optical element, whereby the second capacitor plate is located adjacent the first capacitor plate and separated from the first capacitor by a gap to form a capacitor. An electrical current value associated with the capacitor is measured based on the applied alternating signal. A capacitive reactance value for the capacitor is then measured based on the measured current value and the applied predetermined voltage amplitude. A contaminant on the outer surface of the optical element is detected based on the calculated capacitive reactance, whereby the capacitive reactance varies based on the contaminant entering the gap.

According to at least one other exemplary embodiment, a computer program product for determining contamination over an outer surface of a final stage optical element of an optical system is provided, whereby the computer program product may include a computer readable storage medium readable by a processing circuit and storing instructions for execution by the processing circuit for performing a method. The method may include measuring an alternating signal having a voltage amplitude that is applied between a first capacitor plate located on the outer surface at an outer periphery of the optical element and a second capacitor plate located on the outer surface at the outer periphery of the optical element. The second capacitor plate is located adjacent the first capacitor plate and separated from the first capacitor by a gap to form a capacitor. An electrical current value associated with the capacitor is measured based on the applied alternating signal. A resistance value is calculated based on the measured current value and the measured voltage amplitude. A contaminant on the outer surface of the optical element is then determined based on the calculated resistance value, whereby the resistance value varies based on the contaminant entering the gap.

BRIEF DESCRIPTION OF THE SEVERAL VIEWS OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1A:
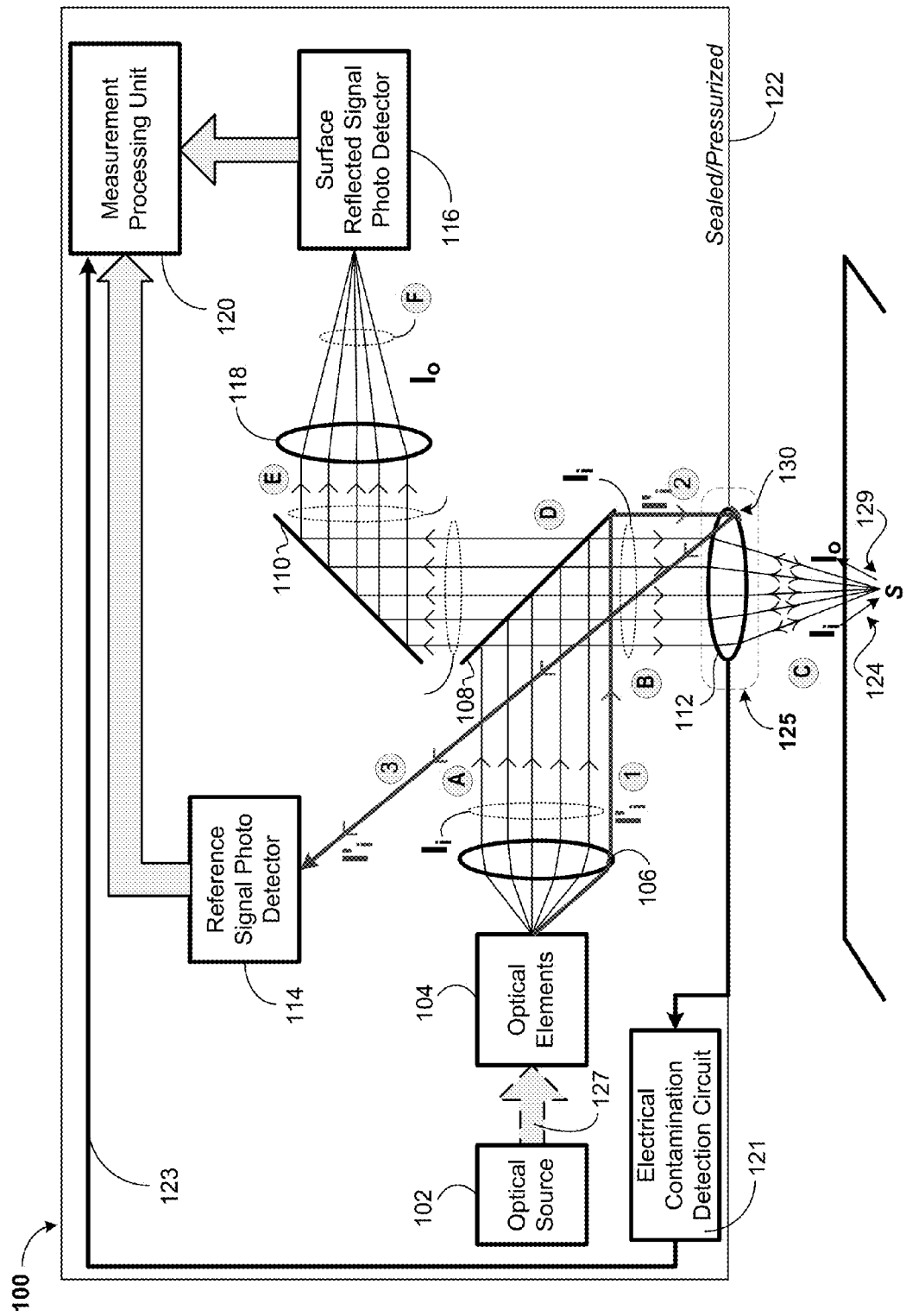
FIG. 1A is an optical system, according to one embodiment.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The following one or more exemplary embodiments describe, among other things, an electronic surface contamination detection apparatus utilized within an optical system for determining measurement errors that may be caused by contaminants coating the one or more optical components of the optical system.

Referring to FIG. 1, an embodiment of an optical system 100 such as a reflectometer is depicted. The optical system 100 may include an optical source 102, one or more optical elements 104 such as lenses, mirrors, splitters, etc., a collimating lens 106, a first splitter 108, a second splitter 110, a final stage optical element 112 such as a focusing lens, a reference signal photodetector 114, a surface reflected signal photodetector 116, a photodetector focusing lens 118, an electrical contamination detection circuit 121, and a measurement processing unit 120. The above-mentioned components 102-120 of the optical system 100 may be housed in a sealed and pressurized enclosure 122 in order to protect these optical components from debris (e.g., gases) that may impact the measurements.

As depicted, a focused incident optical signal $I_i$, as indicated at 124, illuminates a surface under test S, whereby a reflected portion (i.e., from surface S) $I_o$, as indicated by 129, of the focused incident optical signal $I_i$ is used to determine the reflectivity characteristics of the surface under test S. For example, the surface under test S may include a film, dielectric, or any other layer associated with a device such as a manufactured semiconductor structure. By determining the reflectivity of such surfaces S, the characteristics and/or manufacturing tolerances of the films, dielectrics, or other layers may be determined.

In operation, the optical source 102 (e.g., arc lamp, incandescent lamp, fluorescent lamp, etc.) generates an optical signal that may have a wavelength anywhere between ultraviolet (UV) and near infrared (IR) wavelengths, depending on system application. The optical signal output from optical source 102 propagates along path 127 and is received by the one or more optical elements 104 such as lenses, mirrors, splitters, etc. As the optical signal traverses through the one or more optical elements 104, it is received by collimating lens 106. At the collimating lens 106, the incident optical signal, as indicated by $I_i$, is directed towards the beam splitter 108 (Path A), such that the beam splitter 108 reflects the collimated incident optical signal $I_i$ down onto the final stage optical element 112 (Path B), which may, for example, include a focusing lens. Thus, the final stage optical element 112 generates a focused incident optical signal $I_i$ at the surface under reflectivity test S (Path C).

The surface under test S illuminated by the focused incident optical signal $I_i$ may then, based on its characteristic reflectivity (R), reflect anywhere between approximately all (total reflection) to approximately none (total absorption) of the focused incident optical signal $I_i$ at surface S back towards the final stage optical element 112 as a reflected optical signal $I_o$ (Path C). The final stage optical element 112 may then collimate the reflected optical signal $I_o$ from surface S back towards the beam splitter 108 (Path B). At beam splitter 108, the reflected optical signal $I_o$ propagates through the beam splitter 108 (Path D) and onto beam splitter 110. Beam splitter 110 subsequently directs reflected optical signal $I_o$ onto the photodetector focusing lens 118 (Path E) for focusing (Path F) onto the active area of the surface reflected signal photodetector 116. The surface reflected signal photodetector 116 then converts the optical intensity of the reflected optical signal $I_o$ to a magnitude value (i.e., voltage or current value) that is determinative of the detected optical intensity (i.e., power). The magnitude value output from the photodetector 116 is then transmitted to the measurement unit 120 for processing.

Also at the collimating lens 106, a portion of the incident optical signal, as indicated by $I'_i$, is directed towards the beam splitter 108 (Path 1), such that the beam splitter 108 also reflects the portion of the incident optical signal $I'_i$ down onto the final stage optical element 112 (Path 2), which may, for example, include a focusing lens. However, the final stage optical element 112 includes a reflective device 130 having a known reflective surface that reflects the portion of the incident optical signal $I'_i$ back through the final stage optical element 112 and away from the surface under reflectivity test S (Path 3). Since the reflective surface of the reflective device 130 is set to provide maximum reflection, the reflective surface may include a high reflectivity material such as aluminum, silver, or gold with known reflectivity. Region 125, which includes the final stage optical element 112 and reflective device 130, is further described below with the aid of an expanded view of region 125, as depicted in FIG. 1B.

Figure 1B:
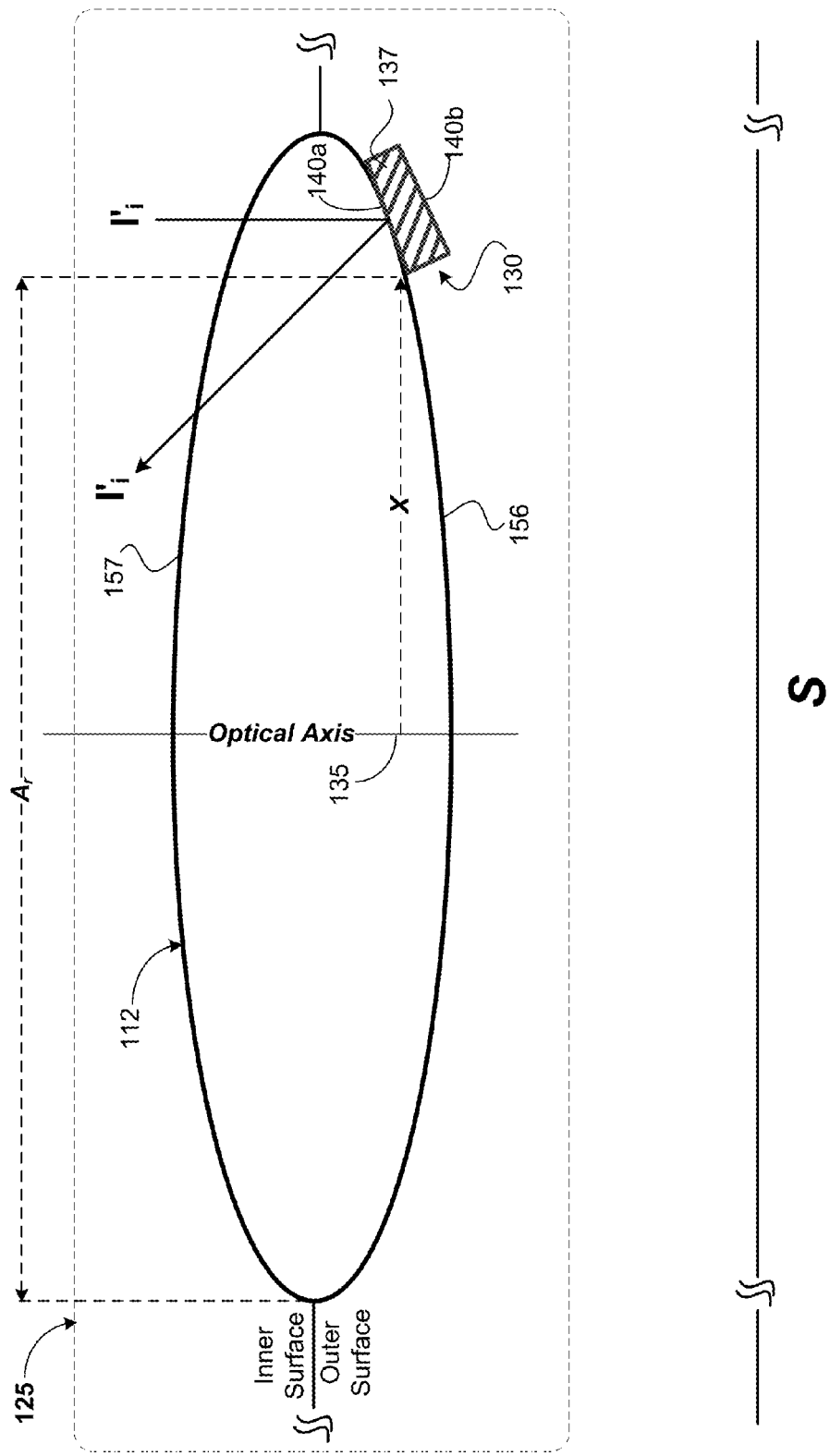
FIG. 1B is an expanded cross sectional view of an optical element having an optical reflective device that is used as an optical reference within the optical system of FIG. 1A, according to one embodiment.

As further shown in FIG. 1A, the portion of the incident optical signal $I'_i$ reflected back through the final stage optical element 112 by reflective device 130 (Path 3) is then received by the active area of the reference signal photodetector 114. The reference signal photodetector 114 then converts the optical intensity of the portion of the incident optical signal $I'_i$ to a magnitude value (i.e., voltage or current value) that is determinative of the detected optical intensity (i.e., power) based on the known reflectivity of reference device 130. The magnitude value output from the photodetector 114 is then transmitted to the measurement unit 120 for processing. The portion of the incident optical signal $I'_i$ detected by reference signal photodetector 114 acts a reference signal, whereby the ratio between the determined magnitude value corresponding to the reflected optical signal $I_o$ and the determined magnitude value corresponding to the portion of the incident optical signal $I'_i$ provides the reflectivity (R) measure of the surface under test S.

The portion of the incident optical signal $I'_i$ detected by reference signal photodetector 114 may be a predetermined/known percentage (e.g., 10%) of the total optical signal that is output from the optical source 102. Therefore, during the calibration of the optical system, this portion (i.e., 10%) of the incident optical signal $I'_i$ detected by the reference signal photodetector 114 may be accordingly weighted (i.e., 90%) to be in proportion with incident optical signal $I_i$ that is applied to surface S. In some implementations, the weighting may be achieved by amplifying the output of photodetector 114 using known photoreceiver circuitry. In other implementations, the weighting may be achieved by the measurement processing unit 120 prior to calculating the reflectivity value (R).

However, during the determination of the reflectivity (R) measure of the surface under test S, there may be a degree of uncertainty leading to a variation in power associated with the measured magnitude of the reflected optical signal $I_o$ and the measured magnitude of the portion of the incident optical signal $I'_i$. For example, due to uncertainties associated with signal loss changes over time (e.g., based on temperature fluctuations, solarization, debris, misalignment etc.) that may be imposed by beam splitters 108 and/or 110, the measured magnitude of the reflected optical signal $I_o$ associated with surface S may deviate from its actual value.

Similarly, due to uncertainties associated with signal loss changes over time (e.g., based on temperature fluctuations, solarization, debris, misalignment, component aging, etc.) that may be imposed by, for example, beam splitter 108, collimating lens 106, the one or more optical elements 104, and/or optical source 102, the measured magnitude of the portion of the incident optical signal $I'_i$ serving as an optical reference signal may deviate from its actual value. Since the reflective device 130 is located at the last stage to reflect back the portion of the incident optical signal $I'_i$ (the optical reference signal), it may be advantageous for the reflective device 130 to provide a reflective surface that is independent of any characteristic changes (e.g., loss) that could apply to the final stage optical element 112. Thus, in this case, any deviations in optical power associated with the portion of incident optical signal $I'_i$ (the optical reference signal) may be attributed to any one of the components (i.e., 102-108) that are upstream from the final stage optical element 112.

As illustrated in FIG. 1B, a cross sectional view of the final stage optical element 112 depicts the reflective device 130 being integrated with the final stage optical element 112 in a manner that mitigates any contamination associated with the reflective device. By removing or reducing such contaminations that can add uncertain variations to the reflectivity R calculation, the reflective device 130 provides a degree of measurement confidence that identifies any upstream fluctuations in power that results from the optical system components and not the reflectivity device 130 itself. As depicted, reflective device 130 is formed on outer surface 156 of the final stage optical element 112, whereby outer surface 156 faces the surface under test S. The reflective device 130 is also formed at a region offset X from the optical axis 135 of the final stage optical element 112. By offsetting X the reflective device 130 relative to the optical axis 135, the majority of the lens area, as indicated by $A_r$, may be devoted to focusing the incident optical signal $I_i$ onto surface S. The reflectivity device 130 includes a reflective surface layer 137 having top and bottom opposing surfaces 140a, 140b. The top surface 140a of the reflective surface layer 137 is deposited on outer surface 156 of the final stage optical element 112, such that top surface 140a is encapsulated between surfaces 156 and 157, while bottom surface 140b of the reflective surface layer 137 remains exposed to the surface under test S. Since the top surface 140a is encapsulated between surfaces 156 and 157, it is shielded from debris and contamination that may result from, for example, the surface under test S. Moreover, outer surface 156 of the final stage optical element 112 is enclosed in a sealed and/or pressurized enclosure. In contrast, the bottom surface 140b of the reflective surface layer 137 that is exposed to the surface under test S may become contaminated by gases that may be released from surface S. This, however, does not affect the reflectivity of top surface 140a, which as depicted, reflects the portion of the incident optical signal I'$_i$ from the outer surface 156 of the final stage optical element 112 back through opposing surface 157 of the final stage optical element 112. In addition to this determination, an exemplary embodiment of an electronic contamination detection system (i.e., FIGS. 1B-1D) may be utilized to detect contamination on the outer surface of the final stage optical element 112. Thus, in combination with reflectivity device 130, the electronic contamination detection system (i.e., FIGS. 1B-1D) determines the measurement integrity of the optical system across the entire optical path leading to the illuminated surface.

Figure 1C:
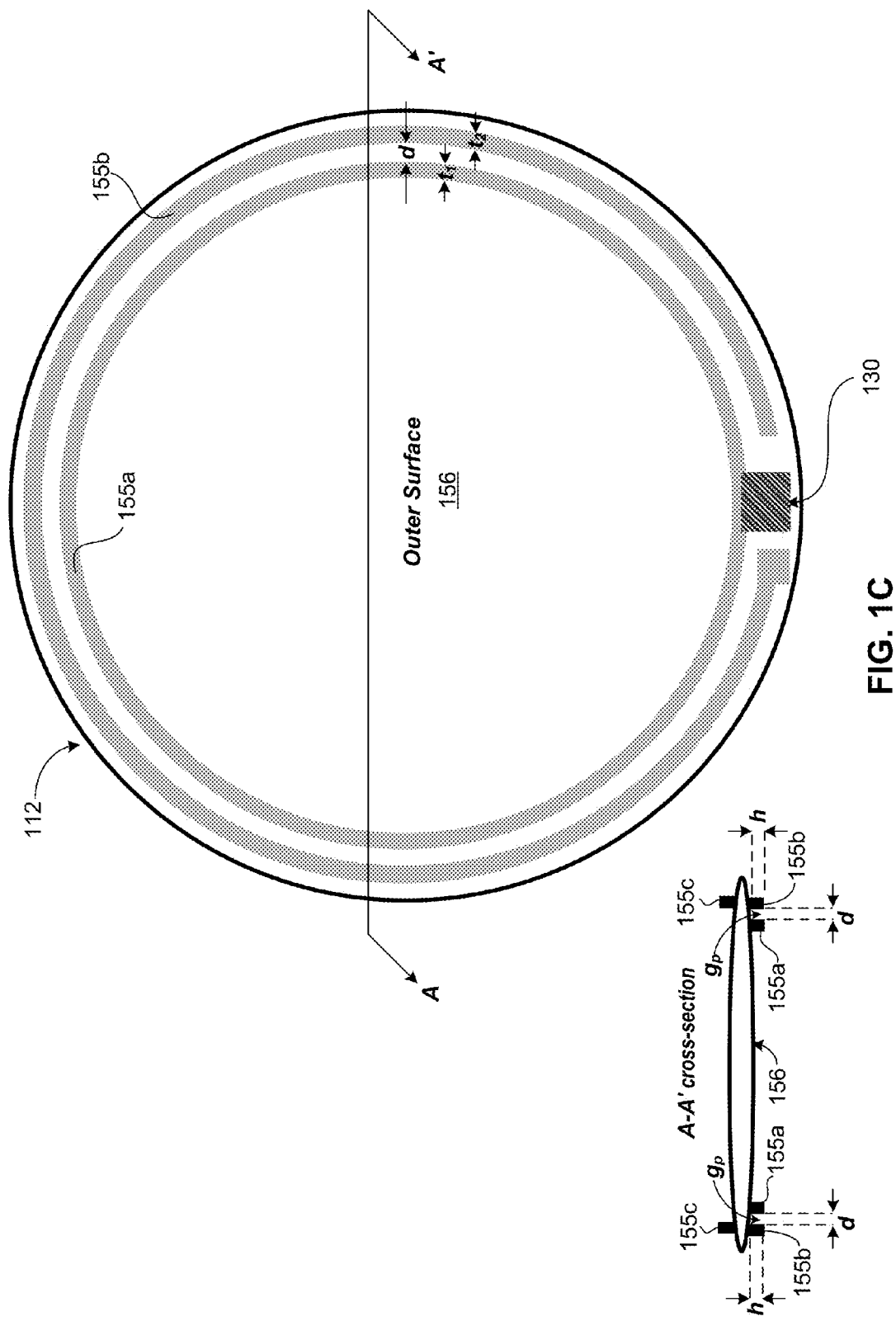
FIG. 1C is a plan view of an outer surface of the optical element depicted in FIG. 1B, which shows a contamination detection capacitor, according to one embodiment.

As illustrated in FIG. 1C, the outer surface 156 plan view of the final stage optical element 112 depicts capacitor plates 155a, 155b being formed on the outer periphery of the final stage optical element 112. The capacitor plates 155a, 155b therefore create a capacitor for detecting debris or contamination on the outer surface of the optical element. The separation d between the capacitor plates 155a, 155b may, for example, be in the range of 0.5-2.0 millimeters (mm). The thickness $t_1$, $t_2$ of the capacitor plates 155a, 155b may be, for example, 1 mm, while the height h of the capacitor plates 155a, 155b, as depicted by the A-A' cross-section view, may be in the region of 2.0 mm. Generally, the height to thickness aspect ratio for the capacitor plates 155a, 155b should be no more than two (2) in order to avoid the capacitor plates 155a, 155b from breaking away from outer surface 156 of the final stage optical element 112 during, for example, cleaning processes. Larger aspect ratios may, however, be contemplated based on the type of cleaning and adhesion used to couple the capacitor plates 155a, 155b to the outer periphery of the final stage optical element 112.

Although the capacitor plates 155a, 155b, 155c are depicted as elongate and extending circumferentially around the outer periphery of the optical element 112, the plates may be any other shape and extend partially around the outer periphery of the optical element 112. In some implementations, the capacitor plates 155a, 155b may, for example, be located at one or more regions of the outer surface 156 of the optical element 112 and be electrically coupled to generate an aggregate capacitance value (i.e., generating parallel capacitors).

Referring to the A-A' cross-section view, the separation d between the capacitor plates 155a, 155b is filled by air, whereby the electric constant ($\in_o$) for air is about 8.854× $10^{-12}$ Fm$^{-1}$. In operation, when no debris or contaminant is covering the outer surface 156 of the optical element 112, air fills the gap $g_p$ separating the capacitor plates 155a, 155b by d. Thus, the capacitance (C) value is determined by:

$$C = \varepsilon_r \varepsilon_0 \frac{A}{d} \quad \text{Equation 1}$$

Where $\in_o$ is the electric constant, $\in_r$ is the relative static permittivity (for an air dielectric $\in_r$=1), A is the surface area of each of the capacitor plates 155a, 155b, and d is the separation between the capacitor plates 155a, 155b. However, when debris or a contaminant covers the outer surface 156 of the optical element 112, the contaminant fills the gap $g_p$ separating the capacitor plates 155a, 155b by d. Thus, depending on the material composition of the contaminant (e.g., from photoresist vapors/gases, dust, silicon particles, etc.), the relative static permittivity may vary between, for example, a factor of about 2 to 100. This indicates that the capacitance value may vary between a factor of 2 to 100 when the outer surface 156 of the optical element 112 is covered by a contaminant. This change in capacitance (C) may, therefore, create enough sensitivity for an electrical contamination detection system 121 (FIGS. 1A & 2) to determine the existence of the outer surface 156 contamination. Furthermore, increasing the surface area of each of the capacitor plates 155a, 155b and reducing the separation between the capacitor plates 155a, 155b may also enhance the detection sensitivity by increasing the capacitance. The capacitor plates 155a, 155b may be formed from, for example, a silver material. As depicted, the inner capacitor plate 155a and the reflectivity device 130 may be integrated as a result of being formed from the same piece of silver. In some implementations, the optical element 112 may include a high numeric aperture lens having a diameter of about 20 mm and a working distance in the micrometer (μm) range.

Figure 1D:
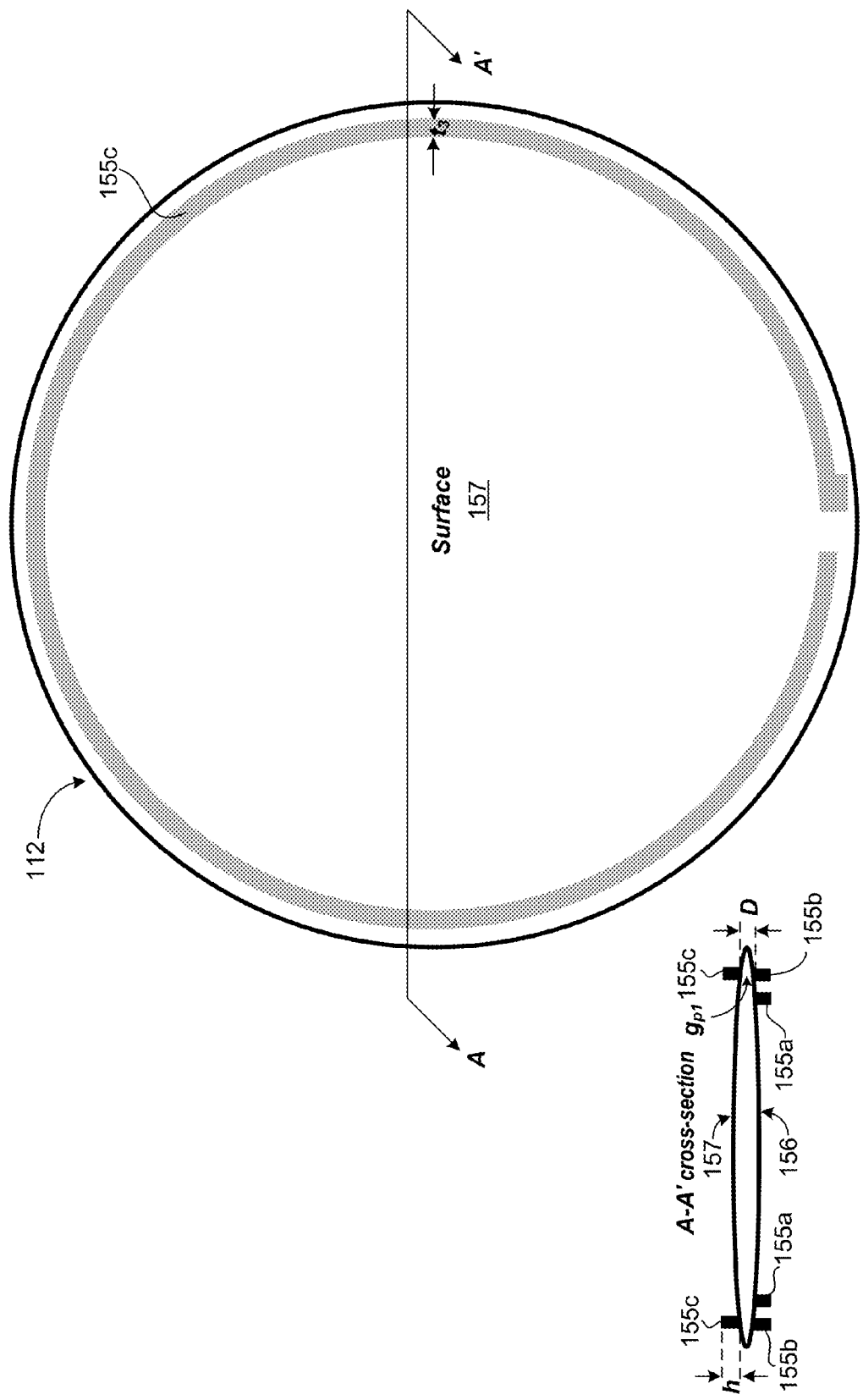
FIG. 1D is a plan view of an inner surface of the optical element depicted in FIG. 1B, which shows a reference capacitor plate, according to one embodiment.
Figure 2:
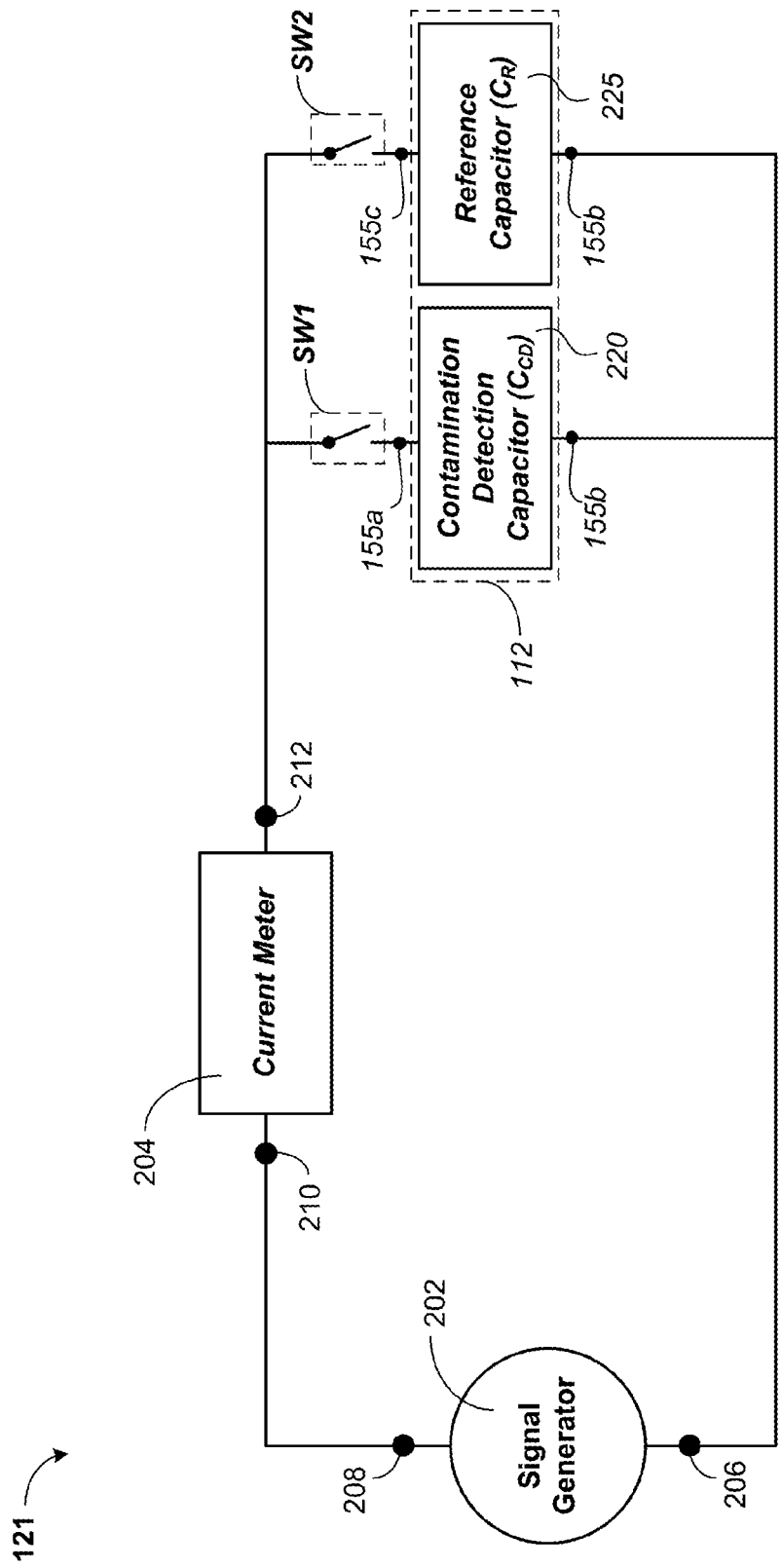
FIG. 2 is block diagram of an electronic contamination detection circuit used in the optical system of FIG. 1A, according to one embodiment.

As illustrated in FIG. 1D, a plan view corresponding to the other surface 157 of the final stage optical element 112 depicts capacitor plate 155c being formed on the outer periphery of the final stage optical element 112. As depicted, surface 157 faces the internal optical elements of the system 100 (FIG. 1A), while outer surface 156 faces an external device or the surface S under test. The thickness $t_3$ of the capacitive plate 155c may be, for example, 1 mm, while the height h of the capacitor plate 155c, as depicted by the A-A' cross-section view, may be in the region of 2.0 mm. Generally, the height to thickness aspect ratio of capacitive plate 155c may be the same as, or similar to, capacitor plate 155b located opposite capacitor plate 155c on other surface 156. As depicted by the A-A' cross-section view of FIG. 1D, capacitor plates 155b and 155c form a reference capacitor that may be utilized for evaluating the operation integrity of the electrical contamination detection system 121 (FIGS. 1A & 2). The operation of the electrical contamination detection system 121 (FIGS. 1A & 2) in conjunction with the capacitor formed by capacitor plates 155a and 155b, and the reference capacitor formed by capacitor plates 155b and 155c, is described below with reference to FIGS. 2 and 3. The separation D between the capacitor plates 155b, 155c may, for example, be in the range of 1.0-3.0 millimeters (mm). Since the gap $g_{p1}$ between the capacitor plates 155b, 155c is formed from the body of the optical element 112, the relative static permittivity ($\in_r$) may be defined by the material constituting the dielectric optical material forming optical element 112. Thus, for a lens optical element 112, the relative static permittivity ($\in_r$) may be that of glass (e.g., $\in_r$=3.7-10). Typically, the capacitance value of the reference capacitor formed by capacitor plate 155b and 155c remains at a fixed value regardless of whether the outer surface 156 of the optical element becomes covered with a contaminant. However, if a change in the capacitance value of the reference capacitor is detected by the electrical contamination detection system 121 (FIGS. 1A & 2), it may be indicative of a failure or change in operating conditions corresponding to the electrical contamination detection system 121 (FIGS. 1A & 2). Therefore, the operational integrity of the electrical contamination detection system 121 (FIGS. 1A & 2) may also be evaluated.

A change in capacitance value may generate a corresponding change in capacitive reactance given by:

$$X_c = \frac{1}{2\pi f C} = \frac{1}{2\pi f \left(\varepsilon_r \varepsilon_0 \frac{A}{d}\right)} = \frac{d}{2\pi f (\varepsilon_r \varepsilon_0 A)} \quad \text{Equation (2)}$$

Whereby capacitance C is replaced by the capacitance formula of Equation 1 and f is the frequency of the signal received by the capacitor C. Accordingly, the electrical contamination detection system 121 depicted in FIG. 2 uses the changes in capacitive reactance value ($X_c$), which follows any changes in capacitance C, to determine the existence of a contaminant over the outer surface 156 (FIG. 1C) of the optical element 112. Referring to Equation 2, as previously described, depending on the material composition of the contaminant (e.g., from photoresist vapors/gases, dust, silicon particles, etc.), the relative static permittivity ($\in_r$) may vary between, for example, a factor of about 2 to 100. This indicates that the capacitance C and, therefore, the capacitive reactance $X_c$ may vary between a factor of 2 to 100.

Referring to FIG. 2, one exemplary embodiment of the electrical contamination detection system 121 may include a signal generation source such as a signal generator 202, an electrical current measurement device such as a current meter 204, switch SW1, and switch SW2. For example, the ground terminal 206 of the signal generator 202 may be electrically coupled to capacitor plate 155b of the contamination detection capacitor ($C_{CD}$) 220 formed by capacitor plates 155a and 155b (also see FIG. 1C). Terminal 208 of the signal generator 202 may be electrically coupled to input terminal 210 of the current meter 204. Output terminal 212 of the current meter 204 couples to capacitor plate 155a (also see FIG. 1C) of the contamination detection Capacitor ($C_{CD}$) 220 via switch SW1. The output terminal 212 of the current meter 204 also couples to capacitor plate 155c of the reference capacitor ($C_R$) 225 formed by capacitor plates 155b and 155c (also see FIG. 1D) via switch SW2.

In a test operation mode, switch SW2 may be periodically closed while SW1 is opened. In this switch configuration, the signal generator 202 generates an alternating signal having a predetermined frequency (e.g., 1 MHz) and voltage value (e.g., 5V). As the alternating signal is applied to the reference capacitor ($C_R$) 225, the current meter 204 measures the current value ($I_r$) drawn by the reference capacitor ($C_R$) 225 based on its capacitive reactance. Under a normal failure-free operation, the current value remains constant at the different measurement periods based on the reference capacitor ($C_R$) 225 having a constant capacitance value. However, if this current value ($I_r$) varies as a result of a change in capacitance value for the reference capacitor ($C_R$) 225, it may be an indication of a circuit failure.

Alternatively, in a contamination detection mode of operation, switch SW2 remains open while SW1 is closed for continuous monitoring. In this switch configuration, the signal generator 202 generates an alternating signal having a predetermined frequency (e.g., 1 MHz) and voltage value (e.g., 5V). As the alternating signal is applied to the contamination detection capacitor ($C_{CD}$) 220, the current meter 204 measures the current value ($I_c$) drawn by the contamination detection capacitor ($C_{CD}$) 220 based on its capacitive reactance.

Under a normal contamination-free operation, the current value ($I_c$) is measured to be at a first value based on the contamination detection capacitor ($C_{CD}$) 220 having a capacitance and, therefore, a capacitive reactance that is based on a relative static permittivity ($\in_r$) of about one (1). As previously described, when there is little to no contamination, the gap $g_p$ (FIG. 1C) between capacitor plates 155a and 155b may be almost entirely filled with air, which includes a relative static permittivity ($\in_r$) of about one (1).

However, when there is contamination covering the outer surface 156 (FIG. 1C) of the contamination detection capacitor ($C_{CD}$) 220, the gap $g_p$ (FIG. 1C) between capacitor plates 155a and 155b may almost entirely be filled with the contaminant, which includes a relative static permittivity ($\in_r$) ranging from, for example, 2-100. Thus, the capacitance (C) and, therefore, the capacitive reactance ($X_c$) may change by a factor of about 2-100 based on the variation in the relative static permittivity ($\in_r$). This change in the capacitance (C) and, therefore, the capacitive reactance ($X_c$) changes the current value ($I_c$) measured by the current meter 204, which may be indicative of a contaminant covering the outer surface 156 (FIG. 1C) of the contamination detection capacitor ($C_{CD}$) 220. Referring to Equation 2, as the capacitance (C) and, therefore, the capacitive reactance ($X_c$) is magnified by a factor of about 2-100, the capacitive reactance ($X_c$) is accordingly reduced by a factor of about 2-100. This in turn may cause the current value ($I_c$) to increase by about 2-100 times, which will be measured by the current meter 204.

The current meter 204 measurements, and the predetermined frequency and voltage settings of the signal generator 202 are coupled to the measurement processing unit 120 (FIG. 1A) by the electrical contamination detection circuit 121 via communications link 123 (FIG. 1A). The communications link 123 may include either a wired or wireless link employing any suitable communication protocol and data communications format.

In alternative embodiments, an electrical contamination detection circuit may include any exemplary electrical circuit or device capable of generating electrical output changes as a function of variations in capacitance. For example, an integrator circuit (not shown) employing an operational amplifier may be used to determine capacitance changes as a function of output rise time or fall time governed by the RC-time-constant of the integrator. Accordingly, the RC-time-constant may be measured and analyzed within measurement processing unit 120 (FIG. 1A) by sampling and digitizing the integrator output. Moreover, in some embodiments, the electrical contamination detection circuit 121 (FIG. 1A) may be included, and thus, integrated within the measurement processing unit 120 (FIG. 1A).

Figure 3:
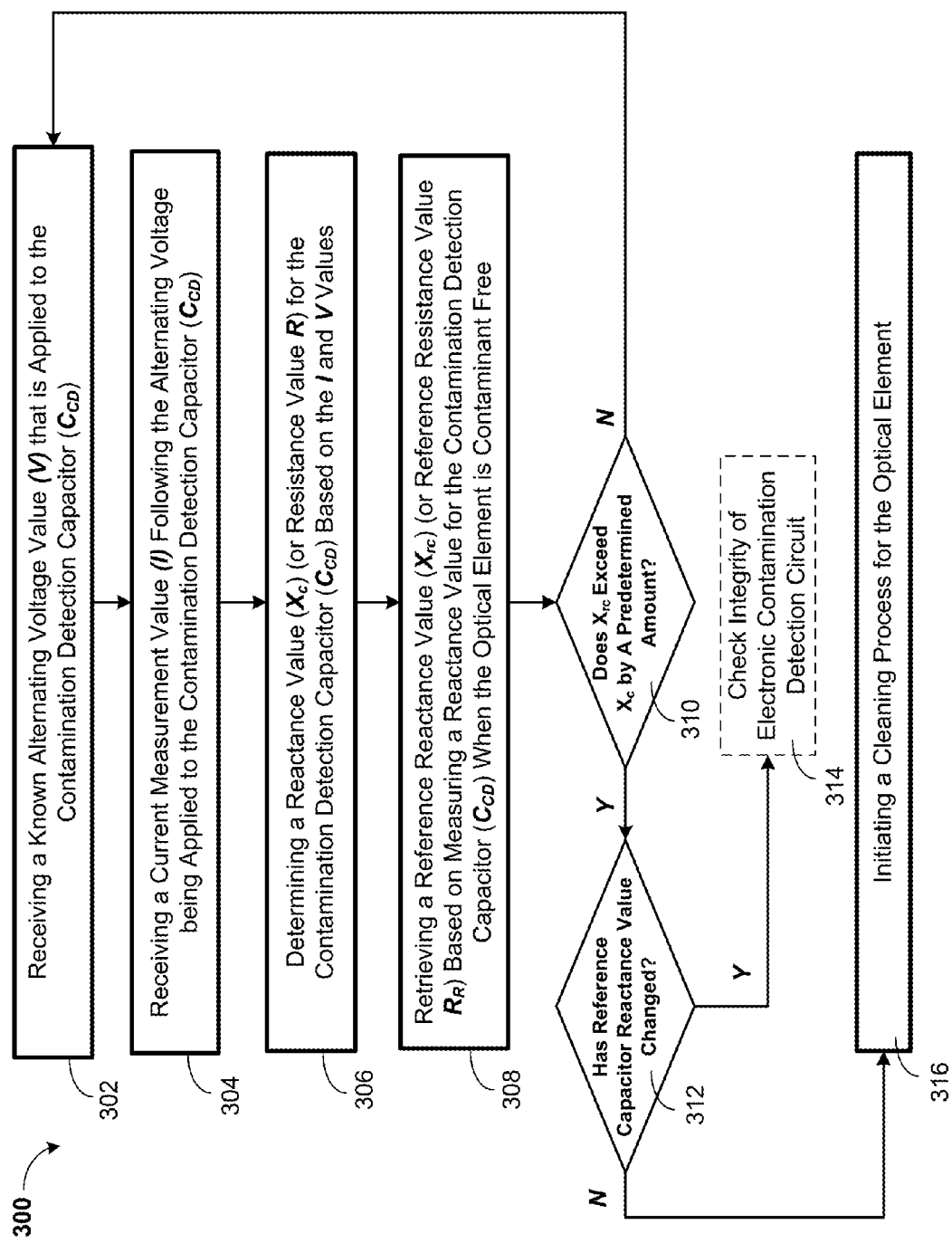
FIG. 3 is a flow chart for an electronic contamination detection process corresponding to a final stage optical element within the optical system of FIG. 1A, according to one embodiment.

FIG. 3 is a flow chart 300 for an electronic contamination detection process corresponding to the outer surface of the final stage optical element 112 within the optical system of FIG. 1A, according to one embodiment. The process of flow chart 300 may be described with the aid of FIGS. 1A-1D and FIG. 2. Moreover, the process of flow chart 300 may be implemented as an executable program within measurement processing unit 120 (FIG. 1A). The process of flow chart 300 may, therefore, also be defined as electronic contamination detection process (ECDP) program 300.

Referring to FIG. 3, at 302, the measurement processing unit 120 receives the voltage (V) and frequency values (f) of a known alternating voltage (e.g., sinusoidal waveform) having a predetermined frequency that is applied to the contamination detection capacitor 220 ($C_{CD}$). In some implementations, the measurement processing unit 120 may set the voltage (V) and frequency values (f) of the known alternating voltage generated by the signal generator 202, which is then applied to the contamination detection capacitor 220 ($C_{CD}$). In such an implementation, the measurement processing unit 120 (FIG. 1A) may control the signal generator 202 via a control bus interface (not shown).

At 304, the measurement processing unit 120 receives a measured current value ($I_c$) from the current meter 204 of the electrical contamination detection circuit 121. At 306, based on the received measured current value ($I_c$) and the received voltage (V) value of the applied alternating signal from signal generator 202, the capacitive reactance $X_c$ of the contamination detection capacitor 220 ($C_{CD}$) is determined. At 308, a reference capacitive reactance $X_{rc}$ for the contamination detection capacitor 220 ($C_{CD}$) is retrieved based on measuring the capacitive reactance of the contamination detection capacitor 220 ($C_{CD}$) when the optical element 112 is contaminant free.

At 310, the capacitive reactance $X_c$ of the contamination detection capacitor 220 ($C_{CD}$) is compared against the reference capacitive reactance $X_{rc}$ of the contamination detection capacitor 220 ($C_{CD}$) using the relationship of Equation (2). If the reference capacitive reactance $X_{rc}$ value exceeds the measured capacitive reactance $X_c$ value by a predetermined amount (e.g., $X_{rc} > X_c$, or $X_{rc} > X_c$+predetermined value), this may be indicative of the outer surface of the 156 of the optical element 112 being covered by a contaminant material. As indicated by Equation (2), with increased contamination covering the outer surface 156 of the optical element 112, the capacitive reactance $X_c$ value reduces based on the relative static permittivity ($\in_r$) increasing. Following this comparison (310), if it is determined that the reference capacitive reactance $X_{rc}$ value exceeds the measured capacitive reactance $X_c$ value, at 312 the integrity of the electrical contamination detection circuit 121 is checked by monitoring the capacitive reactance value of the reference capacitor ($C_R$) 225. This integrity may be evaluated by ensuring that the capacitive reactance value of the reference capacitor ($C_R$) 225 has remained substantially constant and the same as the capacitive reactance value obtained for the reference capacitor ($C_R$) 225 during the error-free operation of the electrical contamination detection circuit 121.

If at 312 it is determined that the capacitive reactance value of the reference capacitor ($C_R$) 225 has changed, the operational integrity of the electrical contamination detection circuit 121 may need to be evaluated (314). However, if at 312 it is determined that the capacitive reactance value of the reference capacitor ($C_R$) 225 has not changed, at 316 a cleaning process for the optical element 112 may be initiated.

However, if at 310 it is determined that the reference capacitive reactance $X_{rc}$ value does not exceed the measured capacitive reactance $X_c$ value by a predetermined amount (i.e., $X_{rc}$ and $X_c$ are approximately the same), this may be indicative of the outer surface of the 156 of the optical element 112 being contaminant-free. Thus, the process returns to 302 and the contamination monitoring process continues.

In some implementations, using the capacitive reactance relationship (i.e., see Equation 2), the relative static permittivity ($\in_r$) and, thus, the type of contaminant may be determined. Specifically, since the capacitive reactance $X_c$ is measured, using the known values of f, d, and A, the $\in_r$ value may be calculated.

According to another embodiment, the process of flow chart 300 may determine the existence of outer surface contaminant coatings using resistance value calculations in place of capacitive reactance. For example, the known or measured alternating voltage V value (i.e., amplitude) and the measured current I value may be used, based on the V/R relation, to determine a resistance value (306). Thus, for example, step 310 may determine whether a retrieved (308) predetermined reference resistance value ($R_R$) exceeds the determined resistance value (R) based on driving the contamination detection capacitor ($C_{CD}$) with an alternating signal.

Figure 4:
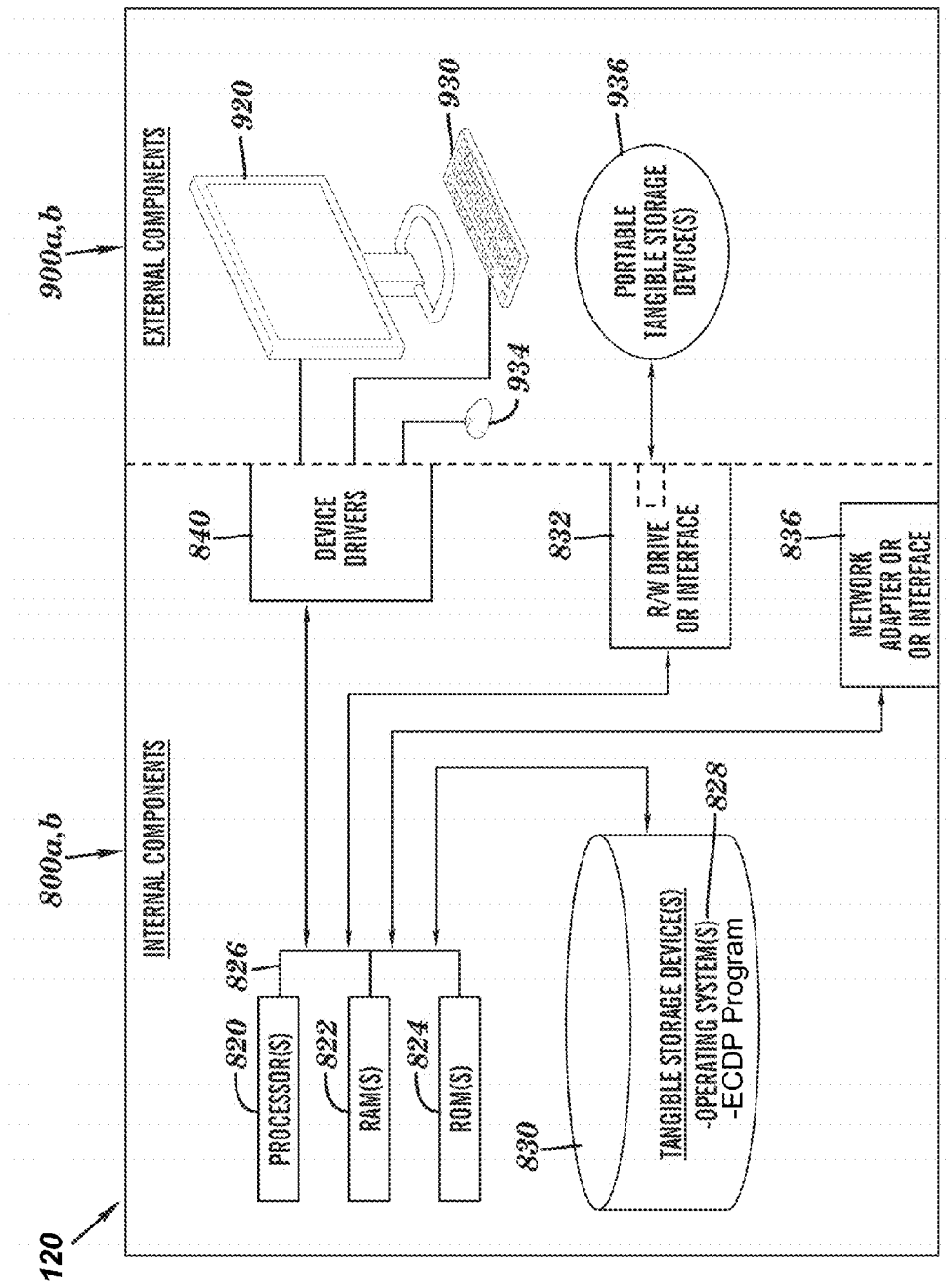
FIG. 4 is a block diagram of hardware and software within the measurement processing unit of FIG. 1A, according to one embodiment.

FIG. 4 shows a block diagram of the components of a data processing system 800, 900, such as measurement processing unit 120 (FIG. 1A) in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may be represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

Measurement processing unit 120 (FIG. 1A) may include respective sets of internal components 800 a, b, c and external components 900 a, b, c illustrated in FIG. 4. Each of the sets of internal components 800 a, b, c includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828 and programs such as the ECDP program 300 corresponding to measurement processing unit 120 (FIG. 1A) is stored on one or more computer-readable tangible storage devices 830 for execution by one or more processors 820 via one or more RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 a, b, c also includes a R/W drive or interface 832 to read from and write to one or more portable computer-readable tangible storage devices 936 such as a CD-ROM, DVD, memory stick, magnetic tape, magnetic disk, optical disk or semiconductor storage device. The optical system processing program 300 (FIG. 3) associated with measurement processing unit 120 (FIG. 1A) can be stored on one or more of the respective portable computer-readable tangible storage devices 936, read via the respective R/W drive or interface 832 and loaded into the respective hard drive 830.

Each set of internal components 800 a, b, c may also include network adapters (or switch port cards) or interfaces 836 such as a TCP/IP adapter cards, wireless wi-fi interface cards, or 3G or 4G wireless interface cards or other wired or wireless communication links. Optical system processing program 300 (FIG. 3), in measurement processing unit 120 (FIG. 1A), can be downloaded to measurement processing unit 120 (FIG. 1A) from an external computer (e.g., server) via a network (for example, the Internet, a local area network or other, wide area network) and respective network adapters or interfaces 836. From the network adapters (or switch port adaptors) or interfaces 836, the optical system processing program 300 (FIG. 3) associated with measurement processing unit 120 (FIG. 1A) is loaded into the respective hard drive 830. The network may comprise copper wires, optical fibers, wireless transmission, routers, firewalls, switches, gateway computers and/or edge servers.

Each of the sets of external components 900 a, b, c can include a computer display monitor 920, a keyboard 930, and a computer mouse 934. External components 900 a, b, c can also include touch screens, virtual keyboards, touch pads, pointing devices, and other human interface devices. Each of the sets of internal components 800 a, b, c also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Aspects of the present invention have been described with respect to block diagrams and/or flowchart illustrations of methods, apparatus (system), and computer program products according to embodiments of the invention. It will be understood that each block of the flowchart illustrations and/or block diagrams, and combinations of blocks in the flowchart illustrations and/or block diagrams, can be implemented by computer instructions. These computer instructions may be provided to a processor of a general purpose computer, special purpose computer, or other programmable data processing apparatus to produce a machine, such that instructions, which execute via the processor of the computer or other programmable data processing apparatus, create means for implementing the functions/acts specified in the flowchart and/or block diagram block or blocks.

The aforementioned programs can be written in any combination of one or more programming languages, including low-level, high-level, object-oriented or non object-oriented languages, such as Java, Smalltalk, C, and C++. The program code may execute entirely on the user's computer, partly on the user's computer, as a stand-alone software package, partly on the user's computer and partly on a remote computer, or entirely on a remote computer or server. In the latter scenario, the remote computer may be connected to the user's computer through any type of network, including a local area network (LAN) or a wide area network (WAN), or the connection may be made to an external computer (for example, through the Internet using an Internet service provider). Alternatively, the functions of the aforementioned programs can be implemented in whole or in part by computer circuits and other hardware (not shown).

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. A contamination detection apparatus, comprising:
an optical element having an outer surface and another surface opposing the outer surface, wherein the outer surface and the another surface are annular;
a first capacitor plate located on the outer surface at an outer annular periphery of the optical element;
a second capacitor plate located on the same outer surface as the first capacitor plate and at the outer annular periphery of the optical element, the second capacitor plate located adjacent the first capacitor plate and separated from the first capacitor plate by a gap to form a capacitor,
wherein a contaminant is electrically detected based on the contaminant entering the gap and varying a capacitance value corresponding to the capacitor;
an electrical detection circuit that electrically detects the varying of the capacitance value corresponding to the capacitor based on a change in reactance of the capacitor; and
a third capacitor plate located on the other surface at the outer annular periphery of the optical element, the third capacitor plate located opposite the second capacitor plate and separated from the second capacitor plate by another gap to form a reference capacitor,
wherein the reference capacitor determines an operational integrity for the electrical detection circuit.

2. The apparatus of claim 1, wherein the optical element comprises an objective lens.

3. The apparatus of claim 1, wherein the electrical detection circuit comprises:
a signal generation source that generates an alternating voltage signal having a predetermined frequency and predetermined voltage amplitude, the signal generation source having a first and a second electrical terminal, the first electrical terminal being coupled to the first capacitor plate and the second electrical terminal being coupled to the second capacitor plate; and
an electrical current measurement device coupled between the first electrical terminal and the first capacitor plate, the electrical current measurement device measuring a current value through the capacitor formed between the first and the second capacitor plate,
wherein the varying of the capacitance value corresponding to the capacitor is detected based on a variation in the measured current.

4. The apparatus of claim 1, wherein the first capacitor plate comprises a first substantially circular elongate plate having a first height value and a first thickness value, the first height value and the first thickness value having a first aspect ratio not exceeding about two.

5. The apparatus of claim 4, wherein the second capacitor plate comprises a second substantially circular elongate plate having a second height value and a second thickness value, the second height value and the second thickness value having a second aspect ratio not exceeding about two.

6. The apparatus of claim 1, wherein the gap includes an air gap, the air gap having a distance value in the range of about 0.5-2.0 millimeters.

7. The apparatus of claim 1, wherein the third capacitor plate comprises a third substantially circular elongate plate having a third height value and a third thickness value, the third height value and the third thickness value having a third aspect ratio not exceeding about two.

8. The apparatus of claim 1, wherein the other gap has a distance value in the range of about 1.0-3.0 millimeters.

9. The apparatus of claim 1, wherein the other gap comprises a material used to form the optical element.

10. The apparatus of claim 9, wherein the material is a dielectric optical material.

11. The apparatus of claim 1, wherein
the first capacitor plate comprises a first substantially circular elongate plate having a first height value and a first thickness value, the first height value and the first thickness value having a first aspect ratio not exceeding about two, and wherein
the second capacitor plate comprises a second substantially circular elongate plate having a second height value and a second thickness value, the second height value and the second thickness value having a second aspect ratio not exceeding about two, and wherein
the third capacitor plate comprises a third substantially circular elongate plate having a third height value and a third thickness value, the third height value and the third thickness value having a third aspect ratio not exceeding about two.

12. A method of determining contamination over an outer surface of a final stage optical element of an optical system, comprising:
applying an alternating signal having a predetermined voltage amplitude to a first capacitor plate located on the outer surface at an outer periphery of the optical element;
applying a ground signal to a second capacitor plate located on the outer surface at the outer periphery of the optical element, the second capacitor plate located adjacent the first capacitor plate and separated from the first capacitor by a gap to form a capacitor;
measuring an electrical current value associated with the capacitor based on the applied alternating signal;
calculating a capacitive reactance value for the capacitor based on the measured current value and the applied predetermined voltage amplitude; and
determining a contaminant on the outer surface of the optical element based on the calculated capacitive reactance, wherein the capacitive reactance varies based on the contaminant entering the gap.

13. The method of claim 12, wherein the contaminant entering the gap decrease capacitive reactance by increasing a capacitance value of the capacitor by increasing the relative permittivity (cr) of the capacitor by a factor of about 2 to about 100.

14. The method of claim 12, further comprising:
applying the alternating signal having the predetermined voltage amplitude to a third capacitor plate located on the inner surface at the outer periphery of the optical element, the third capacitor plate located adjacent the second capacitor plate and separated from the second capacitor plate by another gap to form a reference capacitor;
measuring another electrical current value associated with the reference capacitor based on the applied alternating signal;
calculating another capacitive reactance value for the reference capacitor based on the other measured current value and the applied predetermined voltage amplitude; and
determining an electrical operation integrity for an electrical circuit used in the applying of the alternating signal and the measuring of the other electrical current value, wherein the determined electrical operation integrity is based on the calculated other capacitive reactance value.

15. The method of claim 12, wherein the alternating signal comprises a frequency of about 1-100 MHz.

16. A computer program product for determining contamination over an outer surface of a final stage optical element of an optical system, the computer program product comprising a computer readable storage medium readable by a processing circuit and storing instructions for execution by the processing circuit for performing a method comprising:
measuring an alternating signal having a voltage amplitude that is applied between a first capacitor plate located on the outer surface at an outer annular periphery of the optical element and a second capacitor plate located on the same outer surface as the first capacitor plate and at the outer annular periphery of the optical element, the second capacitor plate located adjacent the first capacitor plate and separated from the first capacitor by a gap to form a capacitor;
measuring an electrical current value associated with the capacitor based on the applied alternating signal;
calculating a resistance value based on the measured current value and the measured voltage amplitude;
determining a contaminant on the outer surface of the optical element based on the calculated resistance value, wherein the resistance value varies based on the contaminant entering the gap;
measuring the alternating signal having the voltage amplitude that is applied to a third capacitor plate located on the inner surface at the outer annular periphery of the optical element, the third capacitor plate located adjacent the second capacitor plate and separated from the second capacitor plate by another gap to form a reference capacitor;
measuring an other electrical current value associated with the reference capacitor based on the applied alternating signal;
calculating an other resistance value for the reference capacitor based on the other measured current value and the applied predetermined voltage amplitude; and
determining an electrical operation integrity for an electrical circuit used in the applying of the alternating signal and the measuring of the other electrical current value, wherein the determined electrical operation integrity is based on the calculated other resistance value.

17. The computer program product of claim 16, wherein the contaminant entering the gap decrease the calculated resistance value.

* * * * *